(12) United States Patent
Mancine et al.

(10) Patent No.: US 10,665,350 B2
(45) Date of Patent: May 26, 2020

(54) COMPUTERIZED DATA PROCESSING SYSTEMS AND METHODS FOR GENERATING GRAPHICAL USER INTERFACES

(71) Applicant: TeleTracking Technologies, Inc., Pittsburgh, PA (US)

(72) Inventors: Nathan Mancine, Cranberry Twp., PA (US); John Rovnan, Gibsonia, PA (US); Jason Harber, Pittsburgh, PA (US)

(73) Assignee: Teletracking Technologies, Inc., Pittsburgh, PA (US)

( * ) Notice: Subject to any disclaimer, the term of this patent is extended or adjusted under 35 U.S.C. 154(b) by 1188 days.

(21) Appl. No.: 14/951,103

(22) Filed: Nov. 24, 2015

(65) Prior Publication Data

US 2016/0147972 A1   May 26, 2016

Related U.S. Application Data

(60) Provisional application No. 62/084,869, filed on Nov. 26, 2014.

(51) Int. Cl.
| | |
|---|---|
| *G16H 80/00* | (2018.01) |
| *G16H 40/63* | (2018.01) |
| *G16H 10/60* | (2018.01) |
| *G06Q 10/10* | (2012.01) |
| *G06Q 50/24* | (2012.01) |

(52) U.S. Cl.
CPC .............. *G16H 80/00* (2018.01); *G06Q 10/10* (2013.01); *G06Q 50/24* (2013.01); *G16H 10/60* (2018.01); *G16H 40/63* (2018.01)

(58) Field of Classification Search
CPC ........ G16H 80/00; G16H 10/60; G16H 40/63; G06Q 10/10; G06Q 50/24
See application file for complete search history.

(56) References Cited

U.S. PATENT DOCUMENTS

| | | | | | |
|---|---|---|---|---|---|
| 2007/0083403 | A1* | 4/2007 | Baldwin | ............... | G06Q 10/10 705/346 |
| 2013/0304485 | A1* | 11/2013 | Khan | ..................... | G06Q 10/10 705/2 |

OTHER PUBLICATIONS

Extended European Search Report for EP Application No. 15196331.1-1958 dated Jan. 5, 2016 (8 pages).

(Continued)

*Primary Examiner* — Linh Giang Le
(74) *Attorney, Agent, or Firm* — Finnegan, Henderson, Farabow, Garrett & Dunner LLP

(57) ABSTRACT

A method for processing data to generate a graphical user interface may include receiving a set of referral requirements for a first department of a facility, wherein the set of referral requirements indicates data requested by the department for making a referral to the first department. The method may also include creating a plurality of data entry fields associated with the set of referral requirements into an electronic form, receiving a referral request directed to the first department, and providing the electronic form. The method may further include processing received data input to the plurality of data entry fields, automatically filling data fields of a referral notification form using the received input, generating a graphical user interface for notification of a referral to the first department, and providing the graphical user interface to the first department.

20 Claims, 9 Drawing Sheets

(56) References Cited

OTHER PUBLICATIONS

The BugzillaTeam: "The Bugzilla Guide—3.0.11 Release", Jan. 31, 2009, pp. 1-137.

* cited by examiner

COMPUTERIZED DATA PROCESSING SYSTEMS AND METHODS FOR GENERATING GRAPHICAL USER INTERFACES

CROSS REFERENCE TO RELATED APPLICATION

This application claims the benefit of priority based on U.S. Provisional Patent Application No. 62/084,869 filed on Nov. 26, 2014, the entire disclosure of which is incorporated by reference.

TECHNICAL FIELD

The subject matter described herein generally relates to electronic data processing systems that generate and provide graphical user interfaces (GUIs) in a network system. The data processing system may coordinate healthcare referrals, placements, bed assignment, and tracking, particularly between healthcare systems or departments/care units that are disparate and often utilize unrelated, uncoordinated information systems.

BACKGROUND

Modern hospitals treat hundreds of patients every day. When a patient arrives, their condition and needs must be evaluated to ensure proper treatment and placement. Sometimes, the patient must meet with multiple physicians located in different hospital units or facilities, requiring the patient to be moved to and from their designated hospital room. Transferring patients between the units often requires synchronizing employee schedules, exchanging personal documents, and ensuring availability and cleanliness of the hospital beds. Due to the vast number of patients and urgency of care, these processes must be performed in a timely and efficient manner. Every minute of time lost for coordinating patient intake, placement, and transfer may significantly impact the hospital's efficiency and the patient's health condition.

Traditional patient intake, placement, and transfer methods are time consuming, prone to error, and significantly underutilize the capabilities of the hospital. Additionally, traditional methods and systems do not provide sufficient patient information and support staff information coordination, resulting in longer staff transition and patient handoff times and decreased efficiency for the health care system. In view of the deficiencies of current systems, there is a need for improved patient intake, placement, and transfer systems.

The disclosure is directed to mitigating or overcoming one or more of the problems set forth above and/or other problems in the prior art.

SUMMARY

In summary, one embodiment provides a method for processing data to generate a graphical user interface, the method comprising: receiving, by a processor from a networked database, a set of referral requirements for a first department of a facility, wherein the set of referral requirements indicates data requested by the first department for making a referral to the first department; creating, by the processor, a plurality of data entry fields associated with the set of referral requirements into an electronic form; receiving, using a network interface, a referral request directed to the first department; providing, using the network interface and in response to the referral request, the electronic form; processing, using the network interface, received data input to the plurality of data entry fields; automatically filling, by the processor, data fields of a referral notification form using the received input; generating, by the processor, a graphical user interface for notification of a referral to the first department; and providing, using the network interface, the graphical user interface to the first department.

Another embodiment provides a method for receiving information through a graphical user interface, the method comprising: providing a placement application on the graphical user interface of a mobile computing device; authenticating, using a processor of the mobile computing device, a user within the placement application; providing a plurality of referral forms for a plurality of departments in a view of the placement application; providing, in response to a selection received from an input device of the mobile computing device, a referral form for a first department; accepting, using the input device of the mobile computing device, referral data entered into one or more data entry fields of the referral form, wherein each of the data entry fields is associated with a predetermined referral criterion chosen by the first department; and transmitting, using a network interface of the mobile computing device, the referral data to the first department.

A further embodiment provides a method for receiving information through a graphical user interface of a computing device, the method comprising: providing a placement application on a graphical user interface of a computing device; authenticating, using a processor of the computing device, a user of a department within the placement application; providing, in a view of the placement application presented on a display of the computing device, a referral notification form from one of a plurality of users; and providing, in response to a selection received from an input device of the computing device, specific referral data derived from the referral notification form, wherein the specific referral data includes data requested by the first department for making a referral Yet a further embodiment provides a method of displaying information through a graphical user interface, the method comprising: providing, on a mobile computing device, the graphical user interface having a placement application; authenticating, using a processor of the mobile computing device, a clinician within the placement application; and providing, in a view of the placement application presented on the graphical user interface of the mobile computing device, specific information derived from a referral issued from one of a plurality of users.

The foregoing summary is illustrative only and is not intended to be in any way limiting. For a better understanding of the embodiments, together with other and further features and advantages thereof, reference is made to the following description, taken in conjunction with the accompanying drawings.

DETAIL DESCRIPTION

Figure 1:
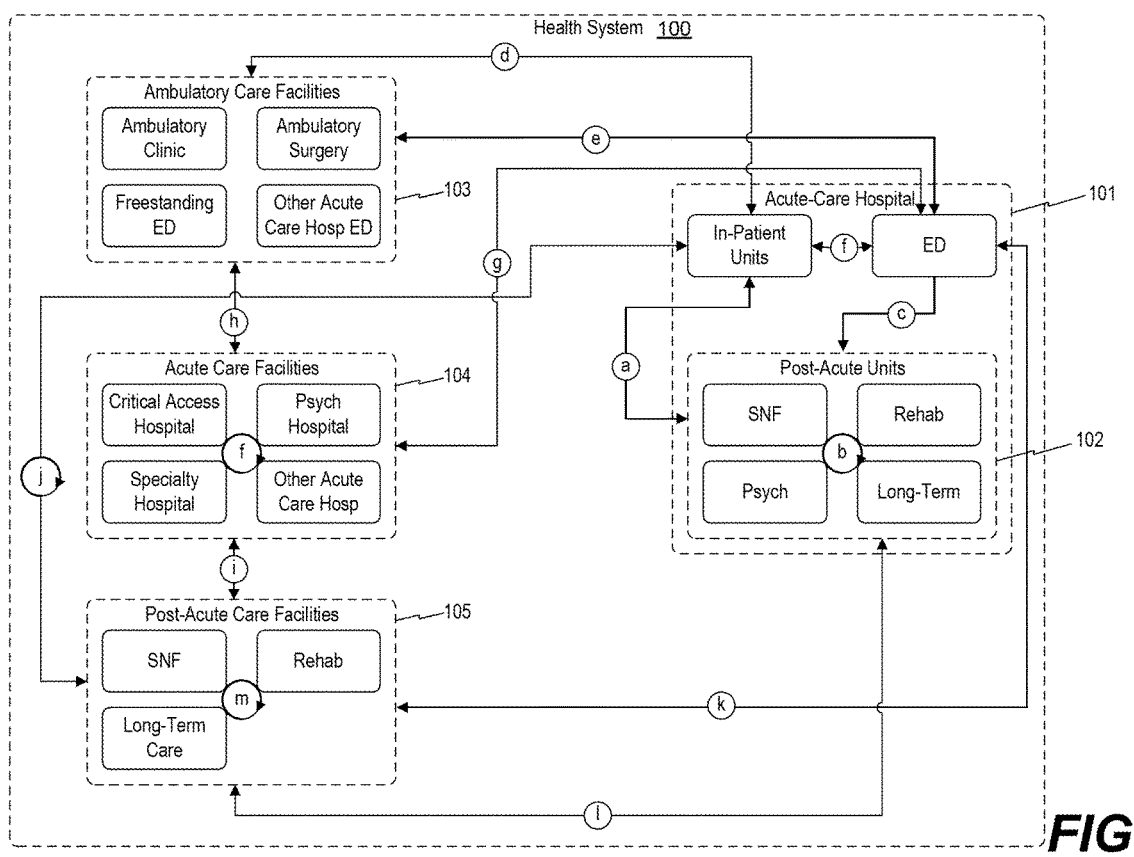
FIG. 1 illustrates an exemplary workflow internal to a health system.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of exemplary embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments may be practiced without one or more of the specific details, or with other methods, components, materials, etcetera. In other instances, well known structures, materials, or operations are not shown or described in detail to avoid obfuscation.

Health systems employ data management systems and techniques that suffer from a lack of organization and commonality. That is, health systems often employ proprietary data management systems that do not or cannot communicate with other proprietary data management systems, either of the same health system or other health systems. Moreover, health system data management suffers from a complete lack of coordination, even in instances where data is communicated between different departments, areas or facilities within the same health system or same physical hospital or building. Furthermore, health systems do not have a mechanism by which data, such as patient data, may be shared with others, even those outside of a particular health system, that are authorized to have access to and use the same.

An embodiment provides a centralized electronic management system that acts as a data aggregator and repository for patient related information and hospital asset information. In one embodiment, the centralized electronic management system collects or receives inputs, for example, regarding patient referral status, asset status, etc., as for example generated and reported by/retrieved from a health system. The centralized electronic management system may also respond to requests, for example, from authorized users, providing data resident therein, for example, patient status information, new referral information, referral template forms, asset status such as bed assignments, bed statuses (pending, clean, occupied, dirty) and the like. The centralized electronic management system may communicate with a variety of devices, including health system data processing systems (e.g., bed management systems) as well as user mobile devices (e.g., smart phones, tablets, laptops, and computer terminals).

An embodiment provides a mechanism that facilitates transfer of a patient into another level or area of care in an inpatient setting, regardless of the patient's origin or destination. For example, the destination may be any patient area within acute and post-acute areas.

An embodiment provides a mechanism that alerts an incoming facility that a patient has been referred to their facility. The incoming facility may, for example, be any type of patient area within ambulatory, acute, and post-acute areas.

An embodiment provides a mechanism that keeps referring clinicians engaged regarding on the status of their patients as they progress through different levels of care.

Utilizing the various embodiments, as further described and explained herein, hospitals and health systems are provided with a mechanism that permits better coordination of patients and their associated care as they transition into and out of the hospital, including internal transfers, for example, between different departments within the health care system or the hospital. Hospitals and health systems are also provided with a mechanism to better coordinate patients and their associated care as they transition out of the hospital.

An embodiment offers healthcare providers with a standard mechanism to refer a patient into an inpatient area or to an outpatient provider.

An embodiment provides referring clinicians with a mechanism for tracking of their patients after they have referred their patient to another care area, for example, referring clinicians may proactively schedule follow-up appointments with their patients following a discharge notification.

An embodiment allows receiving providers to have both better information regarding referrals and better visibility to the patients and their associated needs, resulting in better overall care.

As will be appreciated by reviewing the example embodiments illustrated in the figures, an overall reduction of time associated with transferring/referring a patient from one care area to another is provided, and clinicians for the first time will have access to a centralized coordination system.

The illustrated example embodiments with be best understood by reference to the following description is intended only by way of example, and simply illustrates certain example embodiments.

In order to better appreciate the problems patients and clinicians face, a brief overview of the complexity of the continuum of health care may be of assistance. It should be noted here that a "clinician" is used herein to denote one that provides health care, for example, etc. This is in contrast to the term "patient," which is used herein to denote one that receives treatment.

In health care, the "continuum of care" may be thought of as encompassing ambulatory care, acute care, and post-acute care. Ambulatory care provides personal health care consultations, treatments, or interventions using advanced medical technology or procedures delivered on an outpatient basis. Examples of ambulatory care include but are not limited to primary care physician (PCP) office visits, specialist office visits, ambulatory surgery center treatments, hospital emergency department visits, freestanding emergency department visits, diagnostic/procedural center visits, urgent care visits.

Acute care includes secondary health care, where a patient receives active but short-term treatment for a severe injury or episode of illness, an urgent medical condition, or during recovery from surgery. In medical terms, care for acute health conditions is the opposite from chronic care, or longer term care. Examples of acute care include but are not limited to acute care in a hospital, behavioral health care in a hospital, critical access care in a hospital, specialty care within a hospital (e.g., cardiac, orthopedics, children's care, etc.).

Post-acute care for its part includes a level of medical care designed to improve the transition from the hospital (e.g., an acute care setting) to the community. Examples of post-acute care include but are not limited to in-patient rehabilitation facility treatments, skilled-nursing facility treatments, long-term care hospital treatments, home health care, outpatient rehabilitation center care, outpatient behavioral health facility treatments.

These different care areas may exist in several different modes, including but not limited to part of a health system, an independent part of a health system, a stand-alone facility, an integrated facility or department within an acute care hospital, etc. For any given patient, the health care journey or experience may include interaction with one or more, sometimes many, of the above mentioned areas and modes.

One of an infinite number of examples is a patient that first sees his or her PCP, which then refers the patient to a specialist. The specialist then may want to direct admit the patient, but in the interest of time, directs them to the ED. The ED, for its part, generally has no knowledge that a patient is being sent or why. After going through another assessment in the ED, the patient may be admitted to an inpatient unit in the hospital housing the ED. Due to clinical need, the patient may then be transferred to a specialty hospital located elsewhere. Within that specialty hospital, the patient may be transferred to a rehabilitation unit or department. The patient, after being sent to a rehabilitation facility for additional treatment, then may be discharged to their home and home health may be ordered. The patient may then need a follow-up appointment with both their PCP and the specialist.

In the above example, several referrals were made and accepted, and were accomplished, if done according to currently accepted practice, in a manual manner that is time consuming and error prone. This of course results in longer transition times for the patient. The above example lacks a central coordination mechanism to ensure the relevant patient information is relayed and the appropriate hand-off conversations occur. Several clinicians were involved with the patient and have limited or no visibility to patient after they left their area of care.

Accordingly, an embodiment provides a seamless end-to-end solution for referring/transferring a patient through the different levels of care, across the continuum of care, for example, ambulatory, acute, and post-acute. An embodiment facilitates communication among clinicians regarding the status of the patient.

Figure 2:
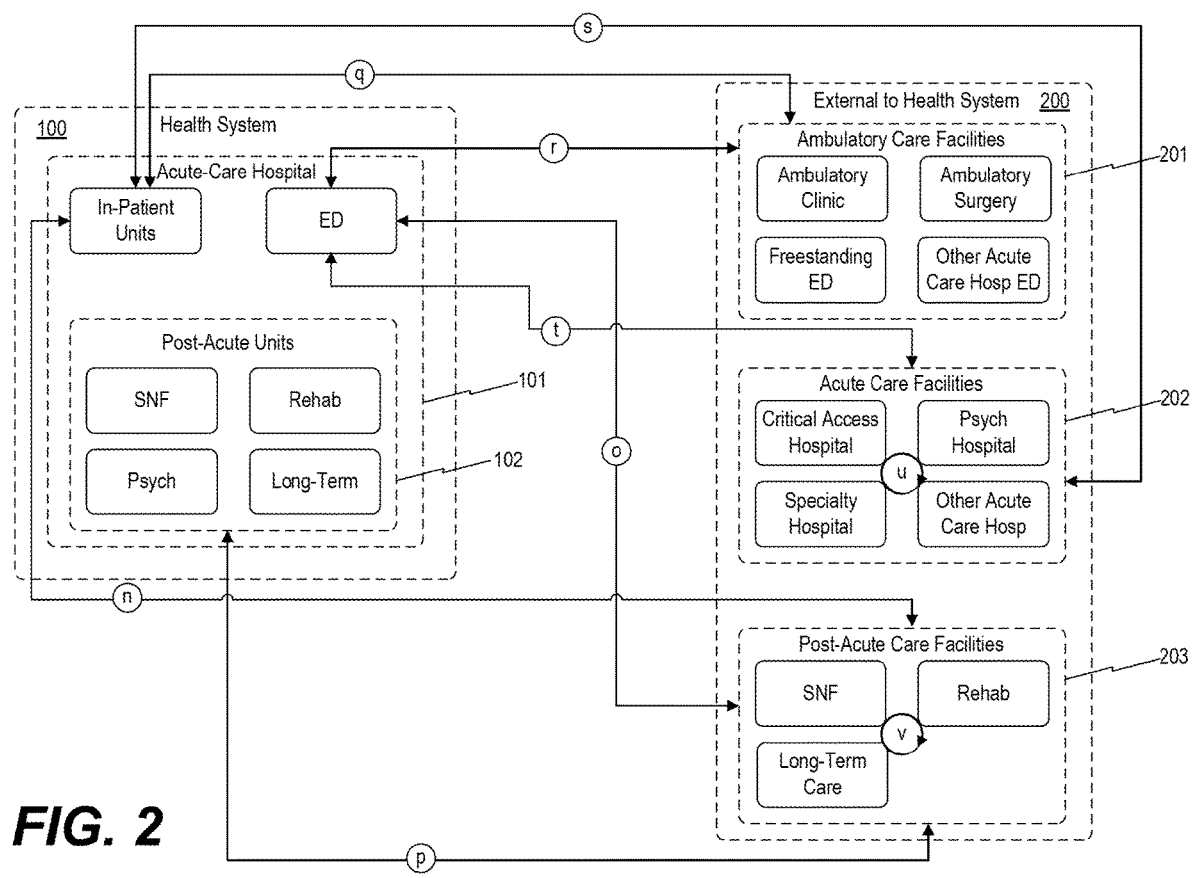
FIG. 2 illustrates an exemplary workflow external to a health system.

Illustrated in the examples of FIG. 1 and FIG. 2 are two diagrams of possible patient workflows/movements internal to a health system 100 (FIG. 1) and external to a health system 200 (FIG. 2). These are new workflows that may be enabled by the existence of a centralized management system, as outlined in FIG. 4.

As illustrated in FIG. 1, health system 100 may include an acute care hospital 101 having post-acute units 102, ambulatory care facilities 103, acute care facilities 104, and post-acute care facilities 105. An exemplary intra-health system transfer (a) may occur between in-patient units within hospital 101 and post-acute units 102. Exemplary transfer (b) may occur between two post-acute units 102, and exemplary transfer (c) may occur between an ED of hospital 101 and post-acute units 102.

Figure 4:
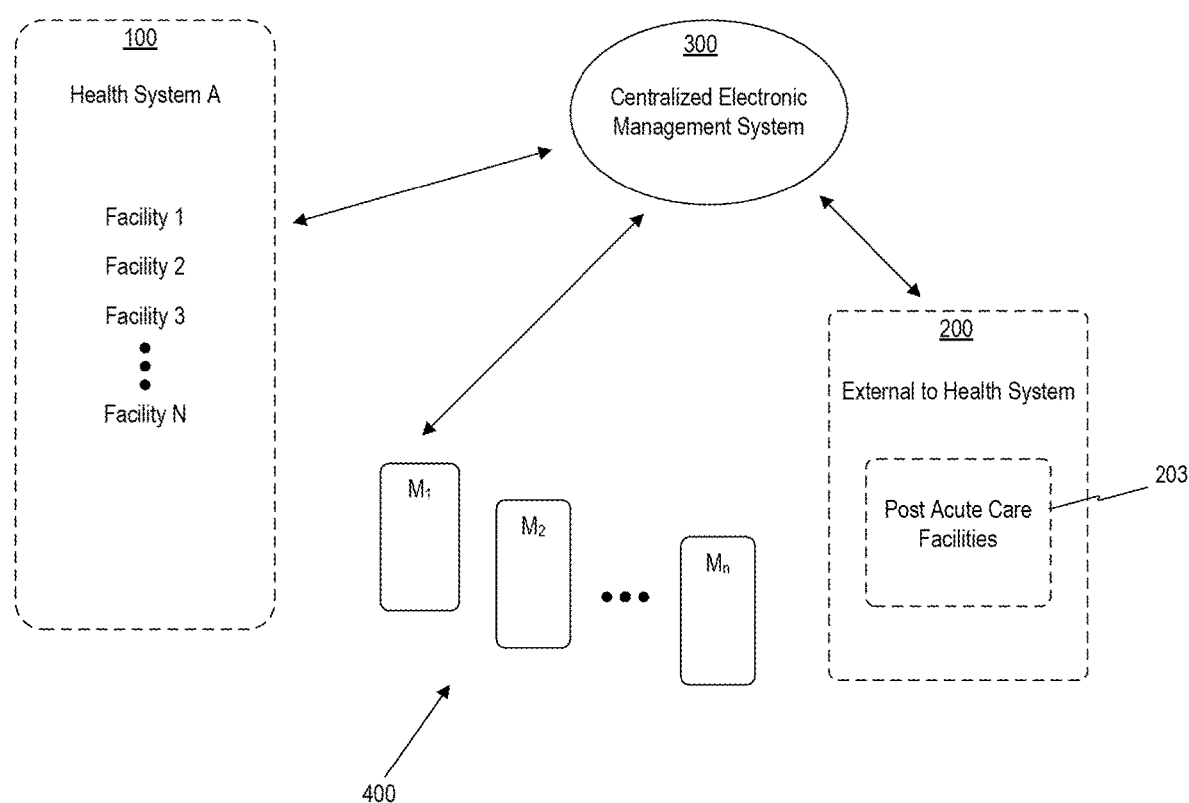
FIG. 4 illustrates an exemplary centralized electronic management system in communication with health system components.

For example, referring to FIG. 4, a centralized electronic management system 300 may receive inputs (or polls to retrieve data) from in-patient units 102, post-acute units and EDs within a health system 100, for example, Health System A. That is, in-patient units, EDs, and post-acute units 102 within Health System A may be organized as separate facilities, for example, Facility 1, Facility 2, Facility 3 . . . Facility N. Often, each facility implements its own data management system, for example, for referring patients, patient intake, etc. However, according to an embodiment, even if disparate systems are currently implemented by the various facilities, centralized electronic management system 300 may aggregate data from each and makes this data available to the various facilities or departments. This may include providing formatted input mechanisms (e.g., fillable fields), applying data processing to proprietary system data to format it for inclusion and use by another proprietary data system, and/or implementation of like data systems within each facility. In this way, each facility's system has access to current patient information in a useable data format, the exchange of which is facilitated by the centralized electronic management system.

Likewise, referring back to FIG. 1, ambulatory transfers (transfers within health system 100) such as transfers (d) from ambulatory care facility 103 to an in-patient unit in the same health system and transfers (e) from ambulatory care facility 103 to an internal ED in the same health system 100 may be facilitated by centralized electronic management system 300. That is, each of the ambulatory care data system, the in-patient unit data system, and the ED data system makes data, for example, patient transfer data, available to centralized electronic management system 300. Centralized electronic data management system 300 in turn communicates this information, with appropriate data processing such as formatting, to the respective department(s) or facilities in a coordinated fashion such that a receiving department is apprised of an in-bound transfer patient, for example, discharged from the ED and transferred into in-patient care, without requiring manual inputs, telephone calls, etc.

Centralized electronic management system 300 likewise facilitates acute care transfers (e.g., within health system 100), including transfers (f) between two acute care hospitals 101 in the same health system 100, transfers (g) between an internal ED and acute care facility 104 in the same health system 100, transfers (h) from ambulatory care facility 103 to acute care facility 104 in the same health system 100, and transfers (i) between acute care facility 104 and freestanding post-acute care facility 105 in the same health system. Post-acute transfer (within the health system) coordinated by centralized electronic management system 300 include transfers (j) between in-patient units and freestanding post-acute care facility 105 in the same health system, transfers (k) between an internal ED and freestanding post-acute care facility 105 in the same health system 100, transfers (l) from a post-acute unit 102 to freestanding post-acute care facilities 105 in the same health system, and transfers (m) between two freestanding post-acute care facilities 105 in the same health system.

Because centralized electronic management system 300 provides data aggregation services, workflows external to a health system are also supported, as outlined generally in FIG. 2. Units external to health system 200 may include ambulatory care facilities 201, acute care facilities 202, and post-acute care facilities 203. By way of example, external transfers (outside of a health system) may include transfers (n) between an in-patient unit and freestanding post-acute care facility 203 outside of the health system, transfers (o) between an internal ED and freestanding post-acute facility 203 outside of the health system, transfers (p) from a post-acute unit 102 to freestanding post-acute care facility 203 outside of the health system, transfers (q) from ambulatory care facility 201 outside of the health system to an in-patient unit, transfers (r) from ambulatory care facility 201 outside of the health system to an internal ED, transfers (s) between an in-patient unit and acute care facility 202 outside of the health system, and transfers (t) between an internal ED and acute care facilities 202 outside of the health system. In this context, transfers (u) between two acute care facilities 202 in the same health system and transfers (v) between two freestanding post-acute care facilities 203 in the same health system may likewise be facilitated by the centralized electronic management system's aggregation and communication of patient data to various entities.

Figure 3:
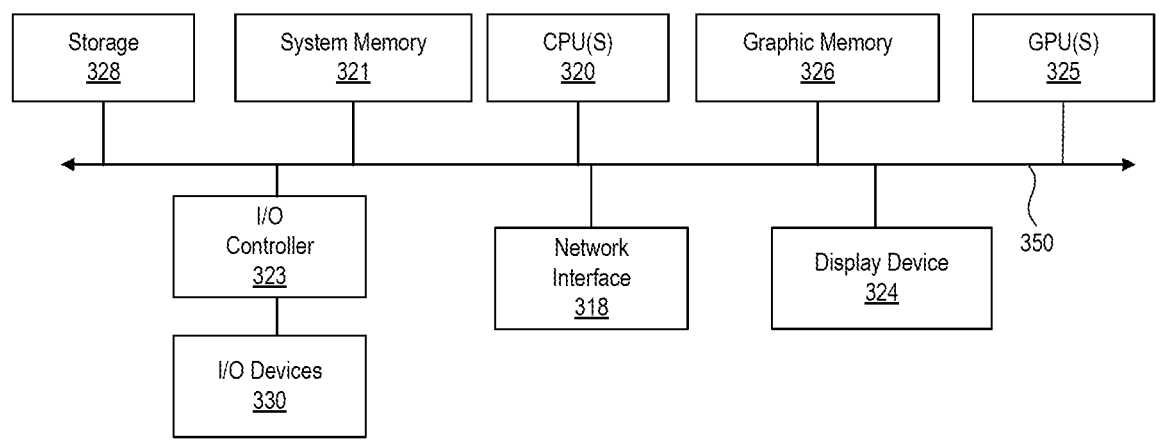
FIG. 3 illustrates an exemplary centralized electronic management system.

FIG. 3 is a block diagram of an exemplary centralized management system 300, consistent with embodiments of the present disclosure. In some embodiments, system 300 may be a server providing the functionality described herein. Further, system 300 may be a second device providing the functionality described herein or receiving information from a server to provide at least some of that information for display.

System 300 may include one or more central processing units (CPUs) 320 and system memory 321. System 300 may also include one or more graphics processing units (GPUs) 325 and graphic memory 326. CPUs 320 may be single or multiple microprocessors, field-programmable gate arrays, or digital signal processors capable of execution sets of instructions stored in a memory (e.g., system memory 321), a cache, or a register. CPUs 320 may contain one or more registers for storing variable types of data including, for example, data, instructions, floating point values, conditional values, memory addresses for locations in memory (e.g., system memory 321 or graphic memory 326), pointers, and counters. CPU registers may include special purpose registers used to store data associated with executing instructions such as an instruction pointer, instruction counter, and/or memory stack pointer. System memory 321 may include a tangible and/or non-transitory computer-readable medium, such as a flexible disk, a hard disk, a compact disk read-only memory (CD-ROM), magneto-optical (MO) drive, digital versatile disk random-access memory (DVD-RAM), a solid-state disk (SSD), a flash drive and/or flash memory, processor cache, memory register, or a semiconductor memory. System memory 321 may be one or more memory chips capable of storing data and allowing direct access by CPUs 320. System memory 321 may be any type of random access memory (RAM), or other available memory chip capable of operating as described herein.

CPUs 320 may communicate with system memory 321 via a system interface 350, sometimes referred to as a bus. GPUs 325 may be any type of specialized circuitry that may manipulate and alter memory (e.g., graphic memory 326) to provide and/or accelerate the creation of images. GPUs 325 may store images in a frame buffer for output to a display device such as display device 324. GPUs 325 may have a highly parallel structure optimized for processing large, parallel blocks of graphical data more efficiently than general purpose CPUs 320. Furthermore, the functionality of GPUs 325 may be included in a chipset of a special purpose processing unit or a co-processor.

CPUs 320 may execute programming instructions stored in system memory 321 or other memory, operate on data stored in memory (e.g., system memory 321) and communicate with GPUs 325 through the system interface 350, which bridges communication between the various components of system 300. In some embodiments, CPUs 320, GPUs 325, system interface 350, or any combination thereof, are integrated into a single chipset or processing unit. GPUs 325 may execute sets of instructions stored in memory (e.g., system memory 321), to manipulate graphical data stored in system memory 321 or graphic memory 326. For example, CPUs 320 may provide instructions to GPUs 325, and GPUs 325 may process the instructions to render graphics data stored in the graphic memory 326. Graphic memory 326 may be any memory space accessible by GPUs 325, including local memory, system memory, on-chip memories, and hard disk. GPUs 325 may enable displaying of graphical data stored in graphic memory 326 on display device 324.

System 300 may include display device 324 and input/output (I/O) devices 330 (e.g., a keyboard, a mouse, or a pointing device) connected to I/O controller 323. I/O controller 323 may communicate with the other components of system 300 via system interface 350. It is appreciated that CPUs 320 may also communicate with system memory 321 and other devices in manners other than through system interface 350, such as through serial communication or direct point-to-point communication. Similarly, GPUs 325 may communicate with graphic memory 326 and other devices in ways other than system interface 350. In addition to receiving input, CPUs 320 may provide output via I/O devices 330 (e.g., through a printer, speakers, or other output devices).

Furthermore, system 300 may include a network interface 318 to interface to a network through a variety of connections including, but not limited to, standard telephone lines, LAN or WAN links (e.g., 802.11, T1, T3, 56 kb, X.25), broadband connections (e.g., ISDN, Frame Relay, ATM), wireless connections, or some combination of any or all of the above. Network interface 318 may comprise a built-in network adapter, network interface card, PCMCIA network card, card bus network adapter, wireless network adapter, USB network adapter, modem or any other device suitable for interfacing system 300 to any type of network 360 capable of communication and performing the operations described herein.

As described herein, various health care staff and clinicians may access data aggregated by centralized electronic management system 300. For example, referring to FIG. 4, clinicians and other staff may access the centralized electronic management system 300 using mobile devices 400 (e.g., $M_1, M_2, \ldots M_n$) by way of an application interface provided, for example, as a mobile application on a smart phone, tablet, or other mobile computing device. User access may be restricted or controlled according to various parameters, for example, user role associated with login credentials. By way of example, a primary care physician may have relatively unrestricted access to patient data and functionality (e.g., ability to transfer a patient), whereas a clinical staff member may have access only to a subset of data or functionality, for example, access a listing of available beds, currently assigned beds, ability to assign an open, clean bed to a patient, etc.

Figure 5:
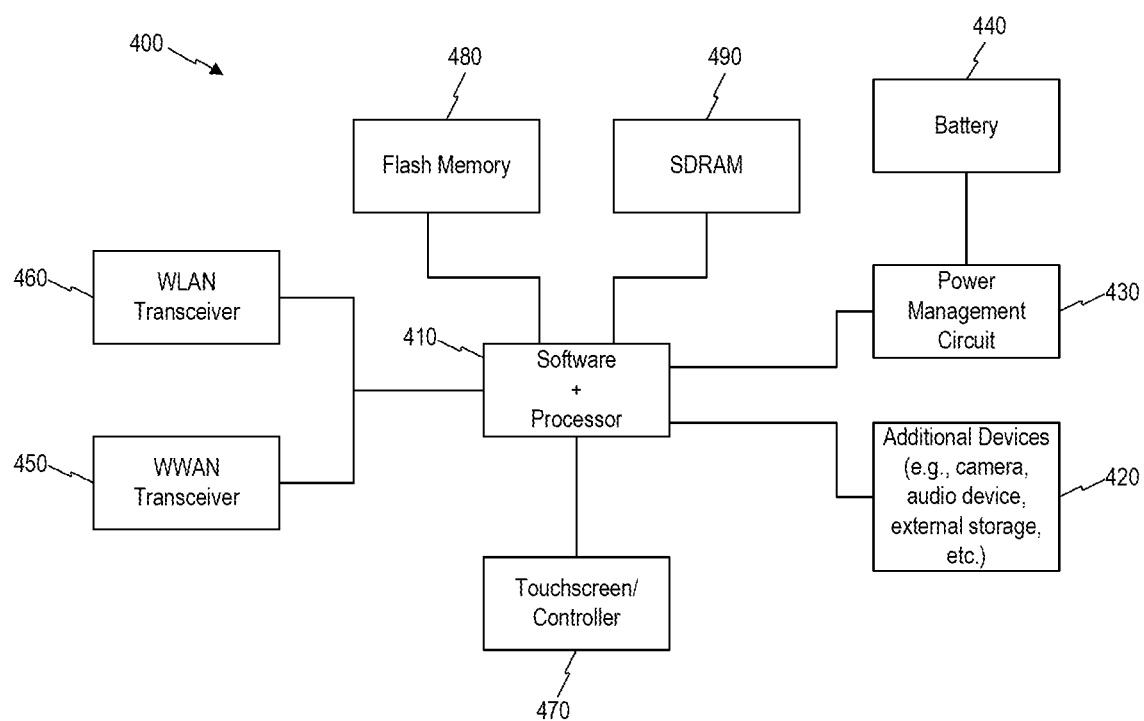
FIG. 5 illustrates exemplary information handling device circuitry.

FIG. 5 is a block diagram of an exemplary mobile device 400, consistent with embodiments of the present disclosure. Mobile device 400 may include software and processor(s) combined in a single circuit 410. Processors may comprise internal arithmetic units, registers, cache memory, busses, I/O ports, etc., as is well known in the art. Internal busses and the like depend on different vendors, but essentially all the additional devices 420 may attach to a single circuit 410. Mobile device 400 may combine the processor, memory control, and I/O controller hub all into a single circuit 410. Also, systems 400 of this type do not typically use SATA or PCI or LPC. Common interfaces, for example, include SDIO and I2C.

In some embodiments, system 300 may generate and provide for display one or more notifications or graphical user interfaces (GUIs) on mobile device 400. Such notifications and GUIs may be a real-world result of data processing processes and functions described herein.

Mobile device 400 may include power management circuit(s) 430, for example, a battery management unit, BMU, which manages power as supplied, for example, via a battery 440, which may be recharged by a connection to a power source (not shown). In at least one design, a single circuit, such as 410, may be used to supply BIOS like functionality and DRAM memory.

Mobile device 400 may include a network interface, including one or more of a WWAN transceiver 450 and a WLAN transceiver 460 for connecting to various networks, such as telecommunications networks and wireless Internet devices, for example, access points.

Mobile device 400 may include a touchscreen/controller 470 for data input and display/rendering. Mobile device 400 may also include various memory devices, for example flash memory 480 and SDRAM 490.

Mobile device 400, as for example outlined in FIG. 4, may be used to implement the coordination and management of the various data types described herein. Moreover, the various embodiments regarding mobile applications may be implemented using circuitry such as outlined in FIG. 5.

As will be appreciated by one skilled in the art, various aspects may be embodied as a system, method or device program product. Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device (328) that are executed by a processor. For example, CPU(s) 320 of system 300, which itself may be distributed, may execute instructions that accept input data, for example, health referral requirements, data related to health referral requests, user logon and selection data, etc., process data, for example, to format disparate health system data to a common format, communicate data to various sources such as remote mobile user devices, health system data management systems, and the like.

Example embodiments are described herein with reference to the figures, which illustrate example methods, devices and program products according to various example embodiments. It will be understood that the actions and functionality may be implemented at least in part by program instructions provided to a processor, such as CPU(s) 320.

Figure 6:
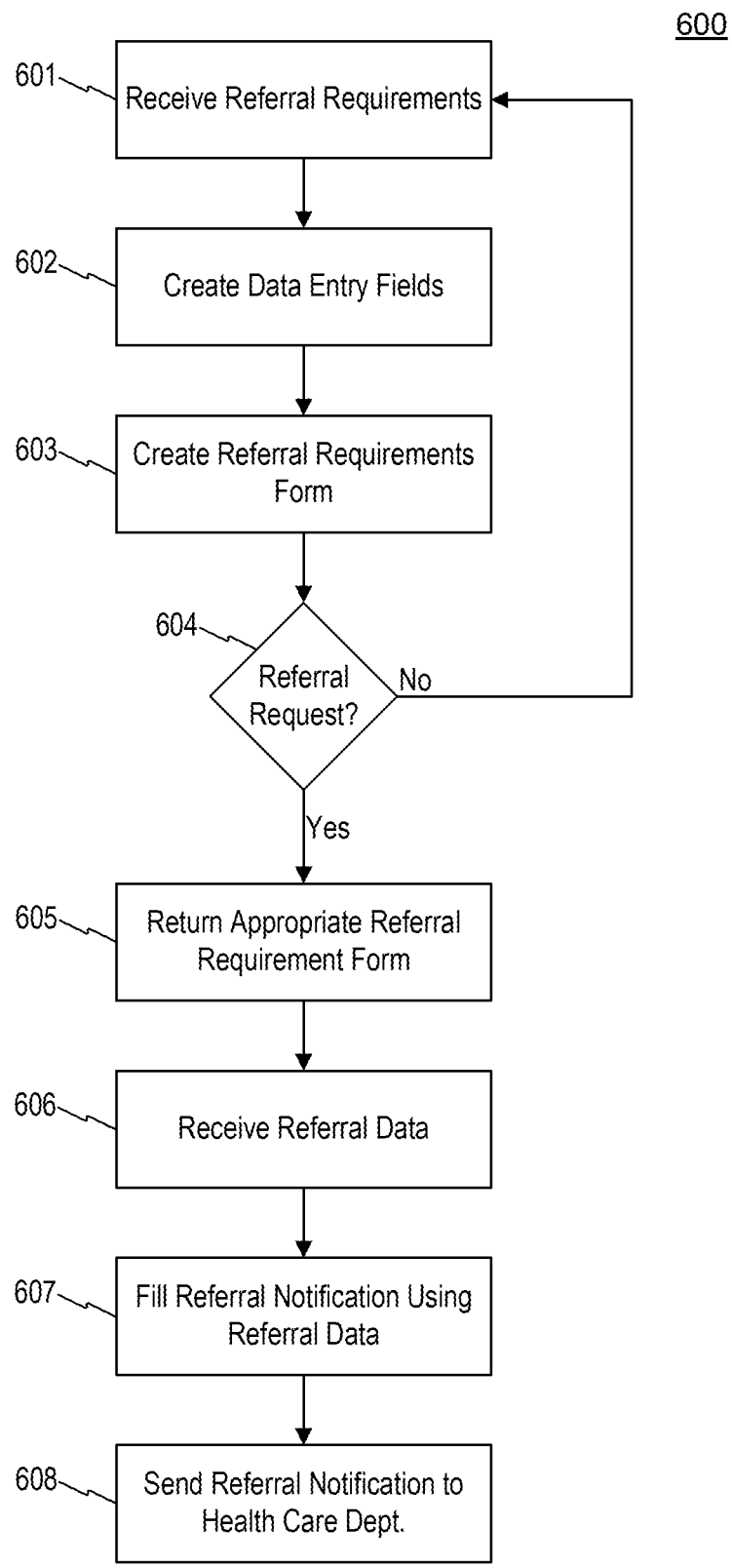
FIG. 6 illustrates an exemplary method of coordinated patient referral.

FIG. 6 illustrates an exemplary method 600 for managing referrals, for example, between the referring clinician, such as a PCP, and a destination health care department, for example, a surgeon working in a surgical department of a hospital. In some embodiments, a set of referral requirements may be received by processor (e.g., CPU 320) from a networked database and the database may be maintained (step 601), for example, by system 300, in order to establish a set of referral requirements for a health care department, for example, a surgical department may receive and list the requirements that are preferred by the department when receiving patient information for a referral.

In some embodiments, a set of referral requirements may include a specific set of information regarding the patient, the referring physician, medical condition information, as well as identifying information (name, date of birth, height, weight, etc.). These requirements may also include formatting requirements, for example, type of data, format of data, organization of data, and the like. Thus, the healthcare department may issue a set of requirements regarding what type of data may be required for a referral, how it should be presented, etc., in order to ensure the department receives the data it needs to complete the referral request.

In some embodiments, system 300 may then create a plurality of data entry fields (step 602) associated with the set of referral requirements, for example, by placing them into an electronic form. The electronic form may include, for example, an application view or browser window that organizes data fields for collecting the referral information, for example, corresponding to the referral requirements of the health care department. Thus, system 300 may create a referral requirement form (step 603) which may be accessed, for example, from within a mobile application downloaded to a clinician's mobile computing device 400 or via a web browser that conveniently lists and organizes the required and/or preferred referral information of the health care department for which the referral is made.

A referring clinician, for example, a PCP, may open the application and select/issue a referral request, for example, where the referral request is directed to the health care department of interest. This may correspond, for example, with a clinician or health care provider selecting a name or icon representing the health care department of interest.

If a referral request is determined ("yes"; step 604), in response system 300 may return appropriate referral requirement form having the appropriate data entry fields given the health care department's requirements and/or preferences (step 605). Once the clinician has access to the referral form, he or she may provide (e.g., input, select, etc.) data for each data entry field such that the form is populated with the referral information.

If a referral request is not determined ("no"; step 604), then process 600 may return to step 601.

In some embodiments, referral information may be received by system 300 (step 606) by, for example, using a network such as the Internet, a private network, a telecommunications network, via network interface 318. System 300 may then automatically fill data fields of a referral notification form (step 607), for example, using the data input by the referring clinician. In some embodiment, the referral notification form and the referral request form may be the same. In the alternative, two different formats may be used.

In any event, because the requirements of the health care department or unit are made known to the referring clinician, for example, via system 300 communicating an appropriate referral notification form, and the appropriate data is received by the health care department, via coordinated communication, the referral information is sent to the health care department in a streamlined fashion (step 608). For example, system 300 may generate, by the processor, a GUI for notification of the referral to the department. System 300 may then provide, using the network interface, the GUI to the department.

Figure 7:
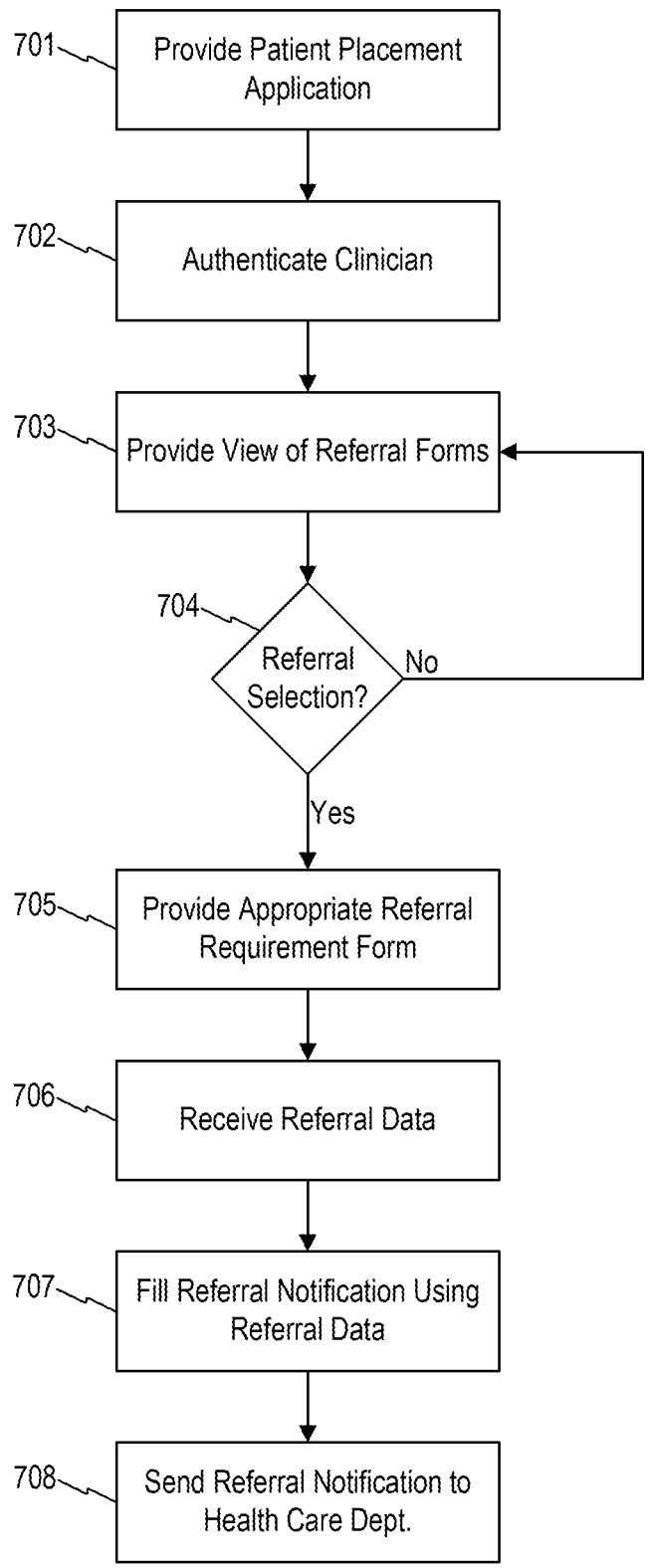
FIG. 7 illustrates an exemplary method of coordinated patient referral using a mobile application.

As may be appreciated from the foregoing, a convenient way to facilitate coordinated information, for example, as outlined with respect to a referral, may be to provide the clinicians with a mobile application. FIG. 7 illustrates an exemplary method 700 for coordinating patient referral through a GUI of a mobile application. As illustrated in FIG. 7, system 300 may provide a patient placement application, for example, on a GUI of a mobile computing device 400, such as a tablet or a smart phone (step 701). A clinician may be authenticated (step 702) within the patient placement application, and thereafter may be provided, for example, in a view of the patient placement application, a plurality of patient referral forms for a plurality of health care departments to which a patient of the clinician may be referred (step 703). The patient placement application, for example, in response to a selection received ("yes"; step 704) from an input device of mobile computing device 400, may provide a referral form for a selected health care department (step 705). If a referral is not selected ("no"; step 704), then process 700 may return to step 703 and continue providing a view of referral forms.

In some embodiments, a clinician may enter, and the patient placement application may accept or receive (step 706), referral data entered into one or more data entry fields of the patient referral form. Again, since the patient referral form is coordinated with the health care department's preferences and/or requirements, each of the data entry fields may be associated with a predetermined referral criterion chosen by the health care department. This data may be transmitted to health care department (step 708), with or without automatic formatting and conversion (step 707).

Figure 8:
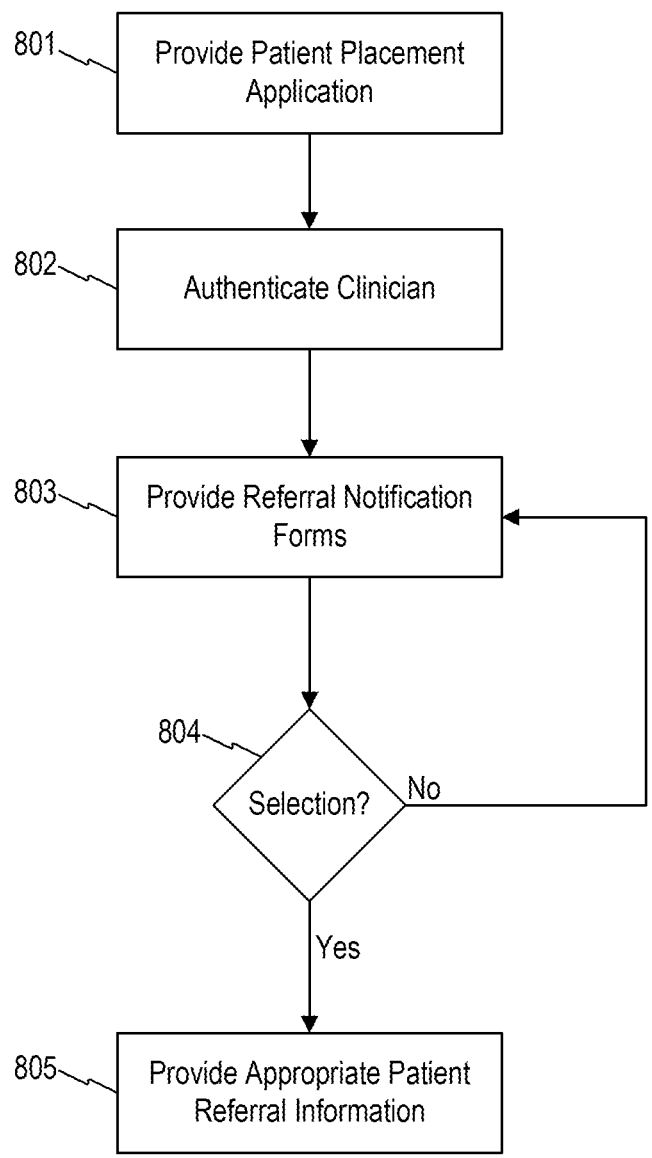
FIG. 8 illustrates an exemplary method of coordinated retrieval of patient referral information.

On the receiving side, for example, at the health care department to which the referral data may be sent, device 300 may facilitate coordinated delivery of properly formatted and organized information, for example, for convenient use by the admitting unit or department. FIG. 8 illustrates an exemplary method 800 of coordinating referrals through a GUI. Method 800 may include providing a patient placement application on the GUI of a computing device (step 801). Access to the. patient placement application may be restricted, for example, by requiring authentication of a clinician of the health care department within the patient placement application (step 802).

Thereafter system 300 may provide (step 803), in a view of the patient placement application, a patient referral notification form from one of a plurality of health care clinicians, for example, the referring physicians. If a selection is made ("yes"; step 804), system 300 may provide patient specific referral data derived from the patient referral notification form. Again, the provisioning of this data stream lines the referral process, as the patient specific referral data provided (step 805) is data requested by the health care department. That is, the patient specific referral data is already complete, formatted and organized to the satisfaction of the department according to its requirements for making a patient referral. Returning to step 804, if no selection is made ("no"; step 804), then system 300 may continue providing referral notification forms (returning to step 803).

Figure 9:
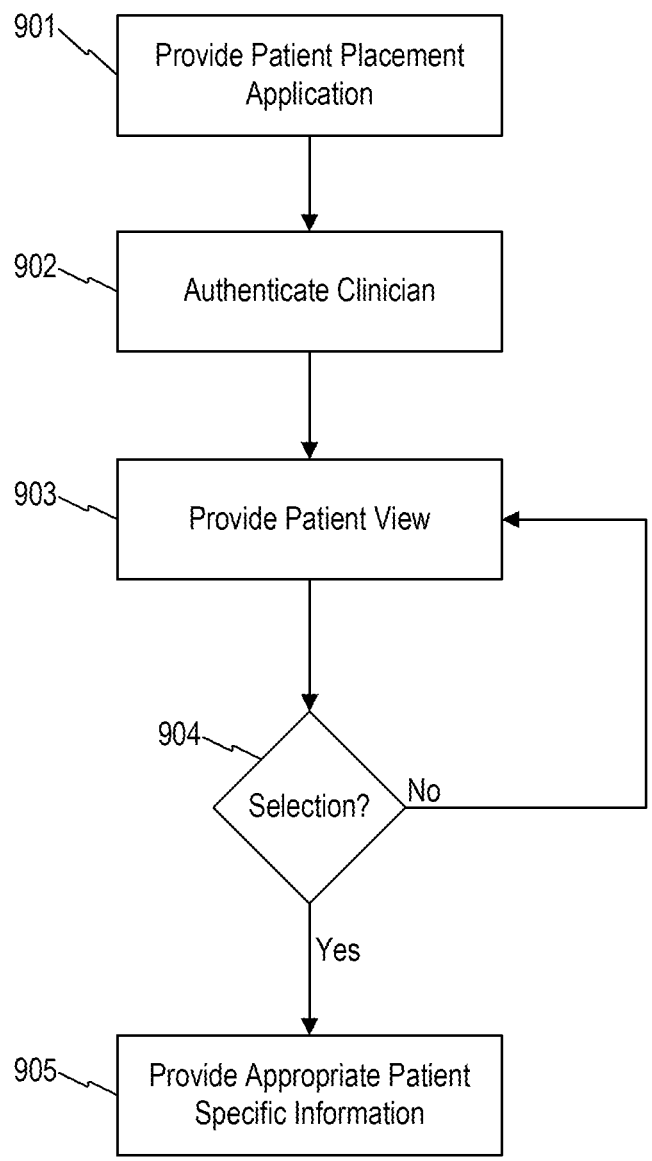
FIG. 9 illustrates an exemplary method of coordinated patient tracking.

FIG. 9 illustrates an exemplary method 900 of coordinating patient tracking through a GUI. As may be appreciated, system 300 may act as a centralized hub or coordinator of information. As such, system 300 may provide a mechanism by which a clinician, for example, a PCP, a specialist, etc. may access data regarding his or her patients. By way of example, system 300 may provide on mobile computing device 400, a patient placement application in step 901.

Access to the application (or sub parts thereof) may be restricted, for example, by authenticating (step 902) a clinician of a health care department, within the patient placement application. Responsive to accessing the application, system 300 may provide (step 903) a patient view, for example, a view of patients that have been referred by (or to) this particular clinician. If the clinician makes a selection of a particular patient ("yes"; step 904), for example, electing a patient's name, patient specific information derived from a patient referral (e.g., issued from one of a plurality of health care clinicians) stored in a database, may be provided at step 905. Returning to step 904, if no selection is made ("no"; step 904), then system 300 may continue providing the patient view (returning to step 903).

In some embodiments, system 300 may permit the clinicians to track the progress of the patients as they transition through their health care journey, even if referred out to or in from different hospitals, health care systems or departments, etc. In some embodiments, system 300 may promote such coordination by acting as a centralized hub where patient information may be placed (e.g., by referring physicians, treating physicians, etc.) and accessed (e.g., by a new department or care facility, by a referred specialist, the original PCP, etc.).

Additionally, an embodiment may provide a clinician such as a healthcare worker charged with assignment of a patient, for example, a new referral, to a bed. Thus, an embodiment may authenticate (step 902) a clinician charged with placing a particular patient in an available bed within the facility. In response to such identification/authentication (step 903), an embodiment may provide in a patient view patient information, for example, referral information such as a type of treatment required.

In step 904, a user may further select to see which bed(s) are currently available or may become available within a given time period, for example, corresponding to the referral patient's arrival. Such information may be gathered from a bed management system of a health care facility, as coordinated by system 300. Thus, the authenticated user may select (step 904) a link or icon for viewing bed availability information (e.g., occupied, clean, dirty, available, pending available, etc.) that may be relevant for the referral patient (e.g., a bed that is or will become available for assignment to the referral patient, the type of bed the referral patient requires, etc.).

Depending on the type of clinician that is authenticated (step 902), other information may be made available, for example, a list of all referred patients for a given time frame, a list of beds and their availability status for a particular department or care area, etc. Accordingly, system 300 may make available other information, for example, hospital information such as bed status information of a bed management system, to a given clinician, for example, based on a role assigned to that clinician and derived from their login to the system. This facilitates coordination of information and makes assignment of beds more efficient.

In some embodiments, a user may assign a particular bed to the referral patient, for example, prior to the patient actually arriving. It may be appreciated that the authenticated user may interface with the system to release a particular bed, for example, for a patient that may be transferring out of a given care area, facility or department. Such information may be made available by an embodiment to connected systems, for example, a bed management system, such that the most up to date information is available to other clinicians and staff.

Given the availability of such information, and its centralized coordination, other healthcare workers may be apprised (e.g., via appropriate communication mechanisms) of various information. For example, a hospital staff member may assign a pending bed to a new referral patient, and this may in turn issue a communication to cleaning staff that this particular bed is a priority item for a referral patient due within a given time frame.

As may be appreciated, many different clinicians and health care entities, as well as patients, benefit from such centralized management. For example, a referring clinician is conveniently apprised of referring options and requirements of each (in terms of referral data required, etc.). Likewise, the department to which the patient is referred to benefits in receiving the appropriate referral information, which has been organized to their specifications. Furthermore, clinicians that are part of the department or care unit to which the patient may be referred, for example, an on-call physician in a department, may be apprised in real time (or near real time) of the referral, including the appropriate patient specific information, all prior to patient arrival. This may be accomplished via SMS text communication, email, or within an instantiation of the patient placement application, for example, downloaded to the clinician's mobile computing device 400. All of this positively impacts the patient's experience, as they are no longer shuffled between healthcare providers without an overall coordinator keeping track on the patient's progress through the system of treatment.

In some embodiments, the referring clinician may keep track of his or her patient through GUIs generated by system 300 as the patient transitions between and among departments, facilities, etc. For example, a referring clinician may access his or her instantiation of a patient placement application and retrieve tracking information (patient admitted, patient discharged, etc.) as well as medical attribute information (e.g., test results available through EMR data stored by or accessible to an embodiment, visits by other physicians available through updates provided to a repository by the department treating the patient, etc.). This promotes the referring clinician (e.g., PCP) to be active and engaged in coordinating care and keeping the PCP (as well as other clinicians) in the loop with respect to a patient's progress, needs, etc.

In some embodiments, the GUIs may maximize efficiency by providing large amounts of information quickly in an easy-to-read format. The GUIs may provide real time (or near real time) information and generate notifications to the user (such as through push notifications on mobile device 400).

Even though discussed in reference to an embodiment applied to health system, the computerized data processing systems and methods of the disclosure may be applied to other environments, such as offices, schools, hotels, hostels, dorms, etc. For example, system 300 may be configured to manage the receipt of incoming applications in an office environment.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for processing data to coordinate referrals between a plurality of departments, the method comprising:
receiving, by a processor from a networked database, a set of referral requirements for the plurality of departments, the set of referral requirements indicating data requested by each of the departments;
aggregating the set of referral requirements in the networked database;
creating generating, by the processor, an electronic form comprising a plurality of data entry fields selected based on the aggregated set of referral requirements;
receiving, using a network interface, a referral request directed to a first department from the plurality of departments;
providing, using the network interface and in response to the referral request, the electronic form to a first mobile device associated with a second department from the plurality of departments, the electronic form being provided to the first mobile device in a mobile application format;
receiving, using the network interface, inputted data in the plurality of data entry fields of the electronic form;
converting, by the processor, the inputted data to a common format by automatically filling a referral notification form with the referral data, the referral notification form having a different format than the electronic form, the common format being standardized for multiple sources;
generating, by the processor, instructions for displaying a notification graphical user interface in a second mobile device associated with the first department, the notification graphical user interface comprising information in the referral notification form; and
providing, using the network interface, the instructions to the second mobile device in real time using at least one of a push notification, an email, or an SMS text.

2. The method of claim 1, wherein:
the electronic form restricts access thereto via an authentication mechanism; and the electronic form comprises a browser window that organizes the plurality of data fields.

3. The method of claim 1, further comprising:
receiving, by the processor, an indication from the department that the referral request has been accepted; and
maintaining, in the networked database, tracking information regarding an individual, wherein the tracking information is related to the referral request and the indication.

4. The method of claim 3, further comprising:
authenticating a clinician operating the first mobile device, the clinician being associated with the referral request; and thereafter
generating instructions for displaying a tracking graphical user interface comprising instantiation and medical attribute information of the individual, and
providing the instructions for generating the tracking graphical user interface to the first mobile device.

5. The method of claim 3, further comprising:
receiving updated information from the first department regarding the individual; and
maintaining, in the networked database, attribute information regarding the individual,
wherein:
the attribute information is related to the referral request and the indication, and
the attribute information comprises an EMR associated with the individual and visits by other physicians.

6. The method of claim 5, further comprising:
authenticating a user of the first mobile device, the user being associated with the referral request; and thereafter
providing the attribute information to the user.

7. A method for managing referrals through mobile devices, the method comprising:
providing a placement application on a mobile device;
authenticating, using a processor of the mobile device, a user of the placement application;
providing a instructions for displaying a selection graphical user interface to the mobile device, the selection graphical user interface displaying a plurality of referral forms for a plurality of departments in a view of the placement application;
providing, in response to a selection received from an input device of the mobile computing device, an electronic form for a first department;
receiving, from the mobile computing device, referral data entered into one or more data entry fields of the electronic form, each of the data entry fields being associated with a predetermined referral criterion chosen by the first department;
converting the referral data to a common format by automatically filling a referral notification form with the referral data, the referral notification form having a different format than the electronic form, the common format being standardized for multiple sources;
generating instructions for displaying a notification graphical user interface in a remote device associated with the first department, the notification graphical user interface comprising data in the referral notification form; and
transmitting, in real time and using a network interface, the instructions for displaying the notification graphical user interface to the remote device using at least one of: a push notification, an email, or an SMS text communication.

8. The method of claim 7, further comprising:
generating instructions for displaying a tracking graphical user interface comprising placement instantiation and medical attribute information of an individual associated with the referral data;
providing the instructions for displaying the tracking graphical user interface to the mobile device; and
receiving, from the mobile computing device, a selection for tracking information regarding the individual,
wherein the tracking information is related to the referral request.

9. The method of claim 8, further comprising:
receiving, from the mobile computing device, updated attribute information regarding the individual.

10. A method for coordinating referrals between a plurality of departments through graphical user interfaces in mobile devices, the method comprising:
providing a placement application on a first mobile device associated with a first department of the plurality of departments;
authenticating, using a processor of the first mobile device, a user of the placement application;
providing a selection graphical user interface on the first mobile device, the selection graphical user interface displaying a plurality of referral forms for a plurality of departments;
providing, in response to a selection on the selection graphical user interface, an electronic form for a second department of the plurality of departments;
receiving, from the first mobile device, referral data entered in the electronic form;
converting the referral data to a common format by automatically filling a referral notification form with the referral data, the referral notification form having a different format than the electronic form, the common format being standardized for multiple sources;
providing, to a second mobile device associated with the second department, instructions for displaying a notification graphical user interface comprising data in the referral notification form; and
providing, in response to a selection received from an input device of the second mobile device, specific referral data derived from the referral notification form,
wherein the specific referral data includes data requested by the second department for making a referral.

11. The method of claim 10, further comprising:
generating instructions for displaying a tracking graphical user interface comprising placement instantiation and medical attribute information of an individual associated with the referral data;
providing the instructions for displaying the tracking graphical user interface to the first mobile device; and
receiving, from the first mobile device, tracking information regarding the individual,
wherein the tracking information is related to the referral notification form.

12. The method of claim 11, further comprising:
receiving, from the first computing device, updated attribute information regarding the individual.

13. A method of coordinating referrals between a plurality departments in a health system, the method comprising:
providing, on a first mobile device, a placement application, the first mobile device being associated with a first department of the plurality of departments;
authenticating, using a processor of the first mobile device, a user of the placement application;

providing instructions for displaying a selection graphical user interface to the first mobile device, the selection graphical user interface displaying a plurality of electronic forms, each one of the plurality of electronic forms being associated with at least one of the plurality of departments;

receiving, from the first mobile device, referral data entered into one of the plurality of electronic forms;

converting the referral data to a common format by automatically filling a referral notification form with the referral data, the referral notification form having a different format than the plurality of electronic forms, the common format being standardized for multiple sources;

generating instructions for displaying a notification graphical user interface in a second mobile device, the notification graphical user interface comprising data in the referral notification form, the second mobile device being associated with a second department from the plurality of departments; and providing, in a view of the placement application displayed on the second mobile device, the notification graphical user interface, wherein the notification graphical user interface comprises specific information derived from the referral notification form.

14. The method of claim 13, wherein the specific information comprises at least one of referral information, attribute information, tracking information, or identifying information.

15. The method of claim 1, wherein the plurality of departments comprise an ambulatory facility, an acute facility, and a post-acute facility.

16. The method of claim 15, wherein the common data format is configured to be implemented by proprietary systems of the plurality of departments.

17. The method of claim 1, wherein the electronic form comprises a list of referring options.

18. The method of claim 1, further comprising:
receiving patient and asset information from networked systems for each of the plurality of departments, the patient information comprising referral statuses;
aggregating patient and asset information in the networked data; and
generating a repository accessible directly by each of the plurality of departments.

19. The method of claim 1, further comprising:
determining the referral notification is associated with placing a patient in a bed;
requesting bed availability information from a bed management system of the first department; and
updating the notification graphical user interface to display the bed availability information.

20. The method of claim 1, wherein the set of referral requirements comprise type of data and organization of data attributes specific for each one of the plurality of departments.

* * * * *